(12) United States Patent
Toriumi et al.

(10) Patent No.: US 9,592,033 B2
(45) Date of Patent: Mar. 14, 2017

(54) INFORMATION PROCESSING APPARATUS, SERVER APPARATUS, INFORMATION PROCESSING METHOD, INFORMATION PROCESSING PROGRAM, AND RECORDING MEDIUM RECORDING INFORMATION PROCESSING PROGRAM THEREIN

(71) Applicant: Rakuten, Inc., Shinagawa-ku, Tokyo (JP)

(72) Inventors: Satoko Toriumi, Shinagawa-ku (JP); Fumie Suzuki, Shinagawa-ku (JP); Reina Otsuka, Shinagawa-ku (JP); Mutsumi Fukuda, Shinagawa-ku (JP)

(73) Assignee: Rakuten, Inc., Tokyo (JP)

( * ) Notice: Subject to any disclaimer, the term of this patent is extended or adjusted under 35 U.S.C. 154(b) by 0 days.

(21) Appl. No.: 14/238,675

(22) PCT Filed: Jan. 28, 2013

(86) PCT No.: PCT/JP2013/051738
§ 371 (c)(1),
(2) Date: Feb. 12, 2014

(87) PCT Pub. No.: WO2014/115325
PCT Pub. Date: Jul. 31, 2014

(65) Prior Publication Data
US 2015/0145693 A1    May 28, 2015

(51) Int. Cl.
*G08C 19/12*    (2006.01)
*A61B 10/00*    (2006.01)
(Continued)

(52) U.S. Cl.
CPC ........ *A61B 10/0012* (2013.01); *A61B 5/0008* (2013.01); *A61B 5/746* (2013.01);
(Continued)

(58) Field of Classification Search
CPC ....................................................... G06F 3/041
(Continued)

(56) References Cited

U.S. PATENT DOCUMENTS 5,253,230 A * 10/1993 Kuo ...................... G04C 21/02
368/243
6,882,334 B1 * 4/2005 Meyer ................... G06F 3/0231
340/6.1
(Continued)

FOREIGN PATENT DOCUMENTS

JP    2000-111415 A    4/2000
JP    2010-167043 A    8/2010

OTHER PUBLICATIONS

"Digital Thermometer for women, operational manual", OMRON (Registered Trademark), Online, Jan. 9, 2013.
(Continued)

*Primary Examiner* — Amine Benlagsir
(74) *Attorney, Agent, or Firm* — Sughrue Mion, PLLC (57) ABSTRACT

An information processing apparatus according to the present invention causes an alarm output means to output an alarm at a preset time, causes the alarm output means to stop outputting the alarm when a stop instruction is input by a user while the alarm is being output, and makes a transition to a standby state in which biological information wirelessly transmitted from a measurement instrument can be received in response to the stop of the alarm.

9 Claims, 4 Drawing Sheets

(51) Int. Cl.
*A61B 5/00* (2006.01)
*G01K 1/02* (2006.01)
*G01K 13/00* (2006.01)
*G06F 19/00* (2011.01)

(52) U.S. Cl.
CPC ........... *G01K 1/024* (2013.01); *G01K 13/002* (2013.01); *G06F 19/3406* (2013.01); *G06F 19/3418* (2013.01); *A61B 2010/0019* (2013.01)

(58) Field of Classification Search
USPC ........................................ 340/870.01, 870.17
See application file for complete search history.

(56) References Cited

U.S. PATENT DOCUMENTS

| | | | | |
|---|---|---|---|---|
| 2006/0176167 A1* | 8/2006 | Dohrmann | ........... | G08B 25/001 340/506 |
| 2008/0076572 A1* | 3/2008 | Nguyen et al. | ................. | 463/42 |
| 2008/0119710 A1* | 5/2008 | Reggiardo | .......... | G06F 19/3412 600/365 |
| 2008/0194926 A1* | 8/2008 | Goh | ..................... | A61B 5/0002 600/301 |
| 2008/0300572 A1* | 12/2008 | Rankers | ............. | A61B 5/14532 604/504 |
| 2008/0306437 A1* | 12/2008 | Jacobson et al. | ................ | 604/67 |
| 2009/0156923 A1* | 6/2009 | Power | ................ | A61B 5/14532 600/365 |
| 2010/0062833 A1* | 3/2010 | Mattice et al. | ................. | 463/24 |
| 2010/0164736 A1* | 7/2010 | Byers | ...................... | H04L 12/12 340/657 |
| 2011/0053121 A1* | 3/2011 | Heaton | ............. | A61B 5/14532 434/127 |
| 2011/0071464 A1* | 3/2011 | Palerm | ............... | A61B 5/14532 604/66 |
| 2011/0082711 A1* | 4/2011 | Poeze | ............... | A61B 5/14532 705/3 |
| 2012/0238900 A1* | 9/2012 | Rechberg | ................ | A61B 5/01 600/549 |
| 2013/0137940 A1* | 5/2013 | Schafer | ............. | A61B 10/0012 600/301 |
| 2014/0143940 A1* | 5/2014 | Iuliano et al. | .................... | 2/422 |

OTHER PUBLICATIONS

International Search Report for PCT/JP2013/051738 dated Feb. 19, 2013.

* cited by examiner

INFORMATION PROCESSING APPARATUS, SERVER APPARATUS, INFORMATION PROCESSING METHOD, INFORMATION PROCESSING PROGRAM, AND RECORDING MEDIUM RECORDING INFORMATION PROCESSING PROGRAM THEREIN

CROSS REFERENCE TO RELATED APPLICATIONS

This application is a National Stage of International Application No. PCT/JP2013/051738 filed Jan. 28, 2013, the contents of all of which are incorporated herein by reference in their entirety.

TECHNICAL FIELD

The present invention relates to a technical field of portable terminals or the like capable of receiving biological information wirelessly transmitted from a measurement instrument for measuring biological information such as body temperature.

BACKGROUND ART

As disclosed in Patent Document 1, for example, there is conventionally known a thermometer for measuring and accumulating a basal body temperature of a female and estimating a menstruation cycle from the accumulated basal body temperatures. Further, in recent years, there is known a system for transmitting measurement data measured by a thermometer from the thermometer to a server via a portable terminal such as a smart phone and thereby causing the server to display an expected next ovulation date or an expected menstruation start date on the portable terminal. In this system, the thermometer has a function of recording of a plurality of items of measurement data for 40 days, for example, and the thermometer can collectively transfer the measurement data to the server via the portable terminal on a holiday, for example. When transferring measurement data to the server, a user activates an application program of the portable terminal and logs in to the system, then selects data transfer on a display screen of the portable terminal, and places the thermometer and the portable terminal in the vicinity thereby to transfer basal body temperature data.

CITATION LIST

Patent Document

Patent Document 1: JP 2000-111415 A
Non Patent Document 1: OMRON (registered trademark), Digital Thermometer for women, operation manual, [online], [searched on Jan. 9, 2013] Internet <URL:http://www.healthcare.omron.co.jp/product/basic/178>

SUMMARY OF INVENTION

Technical Problem to be solved by the Invention

However, when a plurality of measurement data cannot be recorded in the thermometer, the measurement data needs to be immediately transmitted from the thermometer to the portable terminal. When a function of predicting a next ovulation date or menstruation start date or the like by analyzing the measurement data is mounted on the portable terminal or the server, the portable terminal or the server desirably analyzes the latest measurement data. In such a case, even when the thermometer can record a plurality of measurement data therein, it is desirably that the measurement data is transmitted from the thermometer to the portable terminal immediately after the measurement.

On the other hand, a basal body temperature needs to be measured in bed before arising. However, the user (person to be measured) takes labor to operate the portable terminal and to cause it to receive measurement data from the thermometer immediately after she wakes up. This may be applicable to measurement of blood pressure or the like, for example.

Therefore, the present invention has been made in terms of the above problems, and its object is to provide an information processing apparatus, a server apparatus, an information processing method, an information processing program, and a recording medium recording the information processing program therein capable of efficiently reducing user's labor of operation when a portable terminal or the like receives measurement data measured by a measurement instrument.

Solution to the Problem

In order to achieve the above described problems, an invention described according to an exemplary non-limiting embodiment is characterized in that an information processing apparatus includes an output control means that causes an alarm output means to output an alarm at a preset time; a stop control means that, when a stop instruction is input by a user while the alarm is being output, causes the alarm output means to stop outputting the alarm; and a transition control means that makes a transition to a standby state in which biological information wirelessly transmitted from a measurement instrument can be received in response to the stop of the alarm.

According to this invention, it is possible to efficiently reduce user's labor of operation when the information processing apparatus receives biological information from the measurement instrument.

An invention described according to an exemplary non-limiting embodiment is characterized in that when the biological information is not received from the measurement instrument within a first predetermined time after the transition to the standby state, the output control means causes to output an alarm again after a second predetermined time.

According to this invention, it is possible to prevent a measurement of biological information from being skipped even when the user falls back to sleep after stopping an alarm, for example.

An invention described according to an exemplary non-limiting embodiment is characterized in that the information processing apparatus further includes a first setting means that sets ON or OFF a re-output function of outputting an alarm again after the second predetermined time after an alarm is stopped, wherein when the re-output function is set ON, if the biological information is received from the measurement instrument within the first predetermined time after the transition to the standby state, the first setting means sets OFF the re-output function.

According to this invention, it is possible to reduce labor of operation of setting off the re-output function by the user.

An invention described according to an exemplary non-limiting embodiment is characterized in that the information processing apparatus further includes a measurement means that measure a time until the biological information is received after the alarm is stopped; and a second setting means that sets a transition time until the standby state is brought after the alarm is stopped based on the time measured by the measurement means, wherein when the transition time set by the second setting means elapses after the alarm is stopped, the transition control means makes a transition to the standby state in which the biological information can be received.

According to this invention, it is possible to shorten the standby time until the biological information is actually received after the transition to the standby state, thereby achieving power saving of the power supply.

An invention described according to an exemplary non-limiting embodiment is characterized in that the information processing apparatus further includes a storage means that stores a history of times measured by the measurement means for a plurality of setting contents containing at least an alarm setting time, wherein the second setting means sets the transition time for the setting contents based on the measurement history, and when the transition time corresponding to the setting contents elapses after the alarm output according to the setting contents by the output control means is stopped, the transition control means makes a transition to the standby state in which the biological information can be received.

According to the present invention, it is possible to set a transition time per setting contents, thereby enhancing user's convenience.

An invention described according to an exemplary non-limiting embodiment is characterized in that the information processing apparatus further includes a second setting means that sets a transition time until the standby state is brought after the alarm is stopped based on at least a time required to measure the biological information by the measurement instrument, wherein when the transition time set by the second setting means elapses after the alarm is stopped, the output control means makes a transition to the standby state in which the biological information can be received.

According to this invention, it is possible to shorten the standby time until the biological information is actually received after the transition to the standby state, thereby achieving power saving of the power supply.

An invention described according to an exemplary non-limiting embodiment is characterized in that the alarm is a wake-up alarm.

According to this invention, the user can make a transition to the standby state in which the biological information wirelessly transmitted from the measurement instrument can be received only by instructing to stop the alarm being output immediately after the user wakes up.

An invention described according to another exemplary non-limiting embodiment is characterized in that an information processing method performed by a computer, includes a step of causing an alarm output means to output an alarm at a preset time; a step of, when a stop instruction is input by a user while the alarm is being output, causing the alarm output means to stop outputting the alarm; and a step of making a transition to a standby state in which biological information wirelessly transmitted from a measurement instrument can be received in response to the stop of the alarm.

An invention described according to another exemplary non-limiting embodiment is characterized in that an information processing program is provided for causing a computer to perform: a step of causing an alarm output means to output an alarm at a preset time; a step of, when a stop instruction is input by a user while the alarm is being output, causing the alarm output means to stop outputting the alarm; and a step of making a transition to a standby state in which biological information wirelessly transmitted from a measurement instrument can be received in response to the stop of the alarm.

An invention described according to another exemplary non-limiting embodiment is characterized in that a recording medium computer-readably recording an information processing program therein is provided, the information processing program for causing a computer to perform: a step of causing an alarm output means to output an alarm at a preset time; a step of, when a stop instruction is input by a user while the alarm is being output, causing the alarm output means to stop outputting the alarm; and a step of making a transition to a standby state in which biological information wirelessly transmitted from a measurement instrument can be received in response to the stop of the alarm.

An invention described according to another exemplary non-limiting embodiment is characterized in that a server apparatus to which an information processing apparatus is connectable via a network, includes a storage means that stores an information processing program for causing a computer to perform a step of causing an alarm output means to output an alarm at a preset time, a step of, when a stop instruction is input by a user while the alarm is being output, causing the alarm output means to stop outputting the alarm, and a step of making a transition to a standby state in which biological information wirelessly transmitted from a measurement instrument can be received in response to the stop of the alarm; and a transmitting means that transmits the information processing program to an information processing apparatus in response to a request from the information processing apparatus capable of executing the information processing program.

Effects of the Invention

According to the present invention, it is possible to efficiently reduce user's labor of operation when an information processing apparatus receives biological information from a measurement instrument.

MODES FOR CARRYING OUT THE INVENTION

An embodiment according to the present invention will be described below with reference to the drawings. The embodiment described below is where the present invention is applied to an information providing system.

[1. Structure and Functional Outline of Information Providing System]

Figure 1:
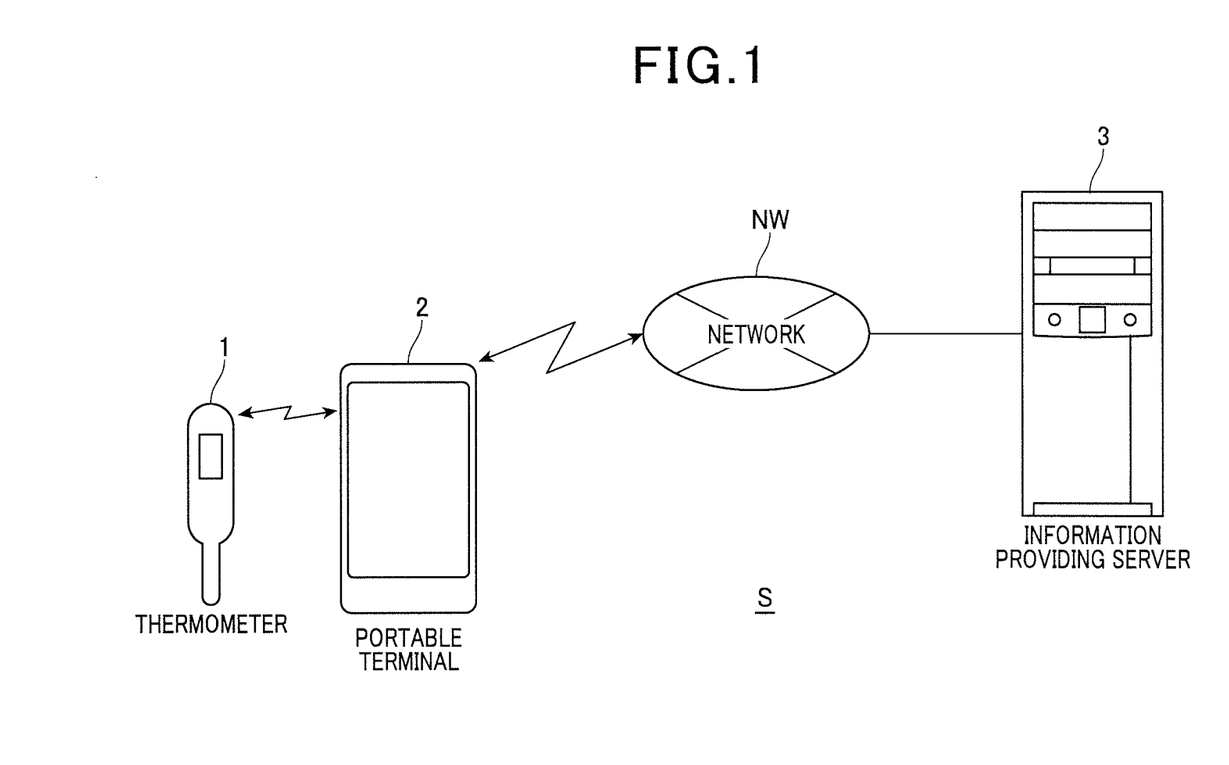
FIG. 1 is a figure illustrating an exemplary outline structure of an information providing system S according to an embodiment.
Figure 2:
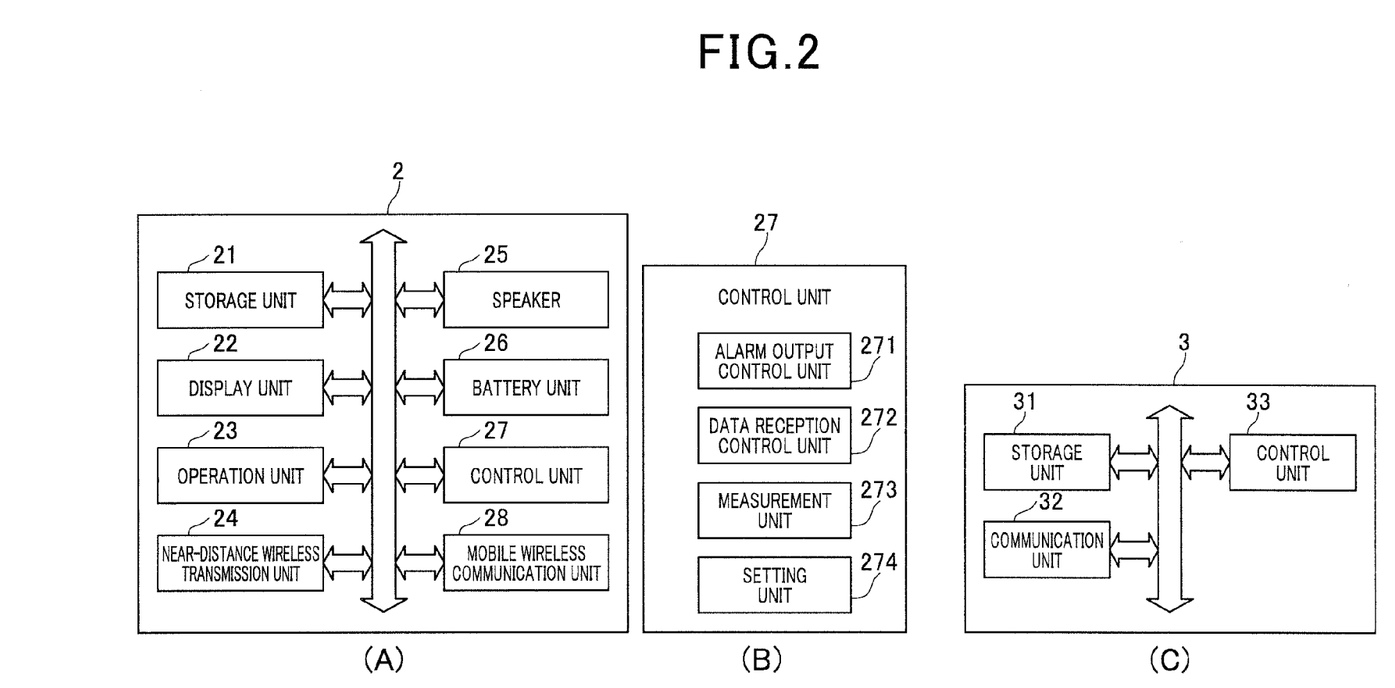
FIG. 2(A) is a figure illustrating an exemplary outline structure of a portable terminal 2.
FIG. 2(B) is a figure illustrating exemplary functional blocks in a control unit 27.
FIG. 2(C) is a figure illustrating an exemplary outline structure of an information providing server 3.

A structure and functions of an information providing system S according to one embodiment of the present invention will be first described with reference to FIG. 1 and FIGS. 2(A) to 2(C) or the like. FIG. 1 is a figure illustrating an exemplary outline structure of the information providing system S according to the present embodiment. FIG. 2(A) is a figure illustrating an exemplary outline structure of a portable terminal 2. FIG. 2(B) is a figure illustrating exemplary functional blocks in a control unit 27. FIG. 2(C) is a figure illustrating an exemplary outline structure of an information providing server 3.

The information providing system S comprises a thermometer 1, the portable terminal 2 and the information providing server 3 as illustrated in FIG. 1. The portable terminal 2 and the information providing server 3 are communicable to each other via a network NW. The network NW is configured of a mobile communication network, Internet or the like, for example.

The thermometer 1 comprises a body temperature measurement unit, a display unit and a near-distance wireless communication unit or the like, the body temperature measurement unit being for measuring a body temperature, the display unit being for displaying a measured body temperature, the near-distance wireless communication unit being for wirelessly transmitting measurement data indicating a measured body temperature. The measurement data is exemplary biological information, and the thermometer 1 is an exemplary measurement instrument. A communication system (communication protocol) in a near-distance wireless communication technique such as Bluetooth (registered trademark) or NFC (Near field communication) is applied to a wireless transmission unit. Alternatively, infrared communication may be applied to the communication system of the wireless transmission unit. When completing a body temperature measurement, the thermometer 1 wirelessly transmits measured measurement data to the portable terminal 2 in a receivable standby state.

The portable terminal 2 comprises a storage unit 21, a display unit 22, an operation unit 23, a near-distance wireless communication unit 24, a speaker 25, a battery (power supply) unit 26, the control unit 27 and a mobile wireless communication unit 28 or the like as illustrated in FIG. 2(A). The portable terminal 2 is an exemplary information processing apparatus according to the present invention. The portable terminal 2 may be provided with a vibrator for vibrating the casing of the portable terminal 2. A portable wireless communication apparatus such as cell phone, Smartphone, tablet, game player is applied to the portable terminal 2. A stationary personal computer may be applied to the portable terminal 2.

The storage unit 21 is configured of a nonvolatile memory or the like such as a flash memory, EEPROM. The storage unit 21 is an exemplary storage means. The storage unit 21 stores OS (Operating System) and "alarm output/data reception control program" or the like therein. The alarm output/data reception control program contains an information processing program according to the present invention. The alarm output/data reception control program is an application program for causing a computer to execute at least a step of causing an alarm output means to output an alarm at a preset time, a step of causing the alarm output means to stop outputting the alarm when the user inputs a stop instruction while the alarm is being output, and a step of transiting to a standby state in which measurement data wirelessly transmitted from the thermometer can be received in response to the stop of the alarm. Herein, the alarm output means is a speaker, for example. The alarm is a sound (may be music). The alarm applied to the present embodiment is a wake-up alarm for waking up (awakening) a sleeping user. An alarm other than the wake-up alarm may be used. The alarm may be vibrations generated by the vibrator of the portable terminal 2. An alarm with light such as LED blinking may be used together. The alarm output/data reception control program can be downloaded from the information providing server 3, for example. The alarm output/data reception control program may be preinstalled in the portable terminal 2. In this case, the portable terminal 2 is provided (lent or sold, for example) to the user while the alarm output/data reception control program is preinstalled in the portable terminal 2. Alternatively, the alarm output/data reception control program may be recorded in a recording medium such as CD (Compact Disc) or DVD (Digital Versatile Disc) and read in the storage unit 21 from the recording medium via a drive. The storage unit 21 also stores therein various items of setting data on alarm setting, measurement data received from the thermometer 1, music data, and the like.

The display unit 22 is configured of a touch panel display or the like, for example. The display displays thereon various screens such as alarm list screen described later. The operation unit 23 is configured of input buttons or the like for user's inputting an operation instruction. The operation instructions include an instruction of displaying various screens, an instruction of setting an alarm, an instruction of stopping the alarm, and the like. The operation unit 23 can input an operation instruction via the touch panel display. A signal indicating an operation instruction input from the operation unit 23 is sent to the control unit 27.

The near-distance wireless communication unit 24 receives measurement data wirelessly transmitted from the thermometer 1 via an antenna. The same communication system as the near-distance wireless communication unit in the thermometer 1, such as a communication with a near-distance wireless communication technique such as Bluetooth (registered trademark) or NFC, or infrared communication or the like, for example, is applied to the communication system of the near-distance wireless transmission unit 24. The speaker 25 outputs an alarm in response to an alarm signal output from the control unit 27. Thereby, the alarm (sound) rings. The alarm signal is an electric signal for controlling an alarm output from the speaker 25. The battery unit 26 is configured of a rechargeable battery or the like. The battery unit 26 supplies power to each component such as control unit 27 provided in the portable terminal 2.

The control unit 27 is configured of CPU (Central Processing Unit), ROM (Read Only Memory), RAM (Random Access Memory) and the like, for example, and has a clock function. The control unit 27 as a computer performs an alarm output/data reception control processing according to the alarm output/data reception control program stored in the storage unit 21, for example. In the processing, the control unit 27 functions as an alarm output control unit 271, a data reception control unit 272, a measurement unit 273, and a setting unit 274 or the like as illustrated in FIG. 2(B). Further, the alarm output control unit 271 is an exemplary output control means and an exemplary stop control means according to the present invention. The data reception control unit 272 is an exemplary transition control means according to the present invention. The measurement unit 273 is an exemplary measurement means according to the present invention. The setting unit 274 is an exemplary first setting means and an exemplary second setting means according to the present invention.

The alarm output control unit 271 causes the speaker 25 to output an alarm at a preset time (set time) (or outputs an alarm signal to the speaker 2 thereby to cause the speaker 25 to output an alarm), and causes the speaker 2 to stop outputting the alarm when the user inputs a stop instruction while the alarm is being output (or stops outputting the alarm signal to the speaker 2 thereby to cause the speaker 2 to stop outputting the alarm). The user's stop instruction can be input from the alarm stop instruction input screen displayed on the display of the display unit 22, for example.

Figure 3:
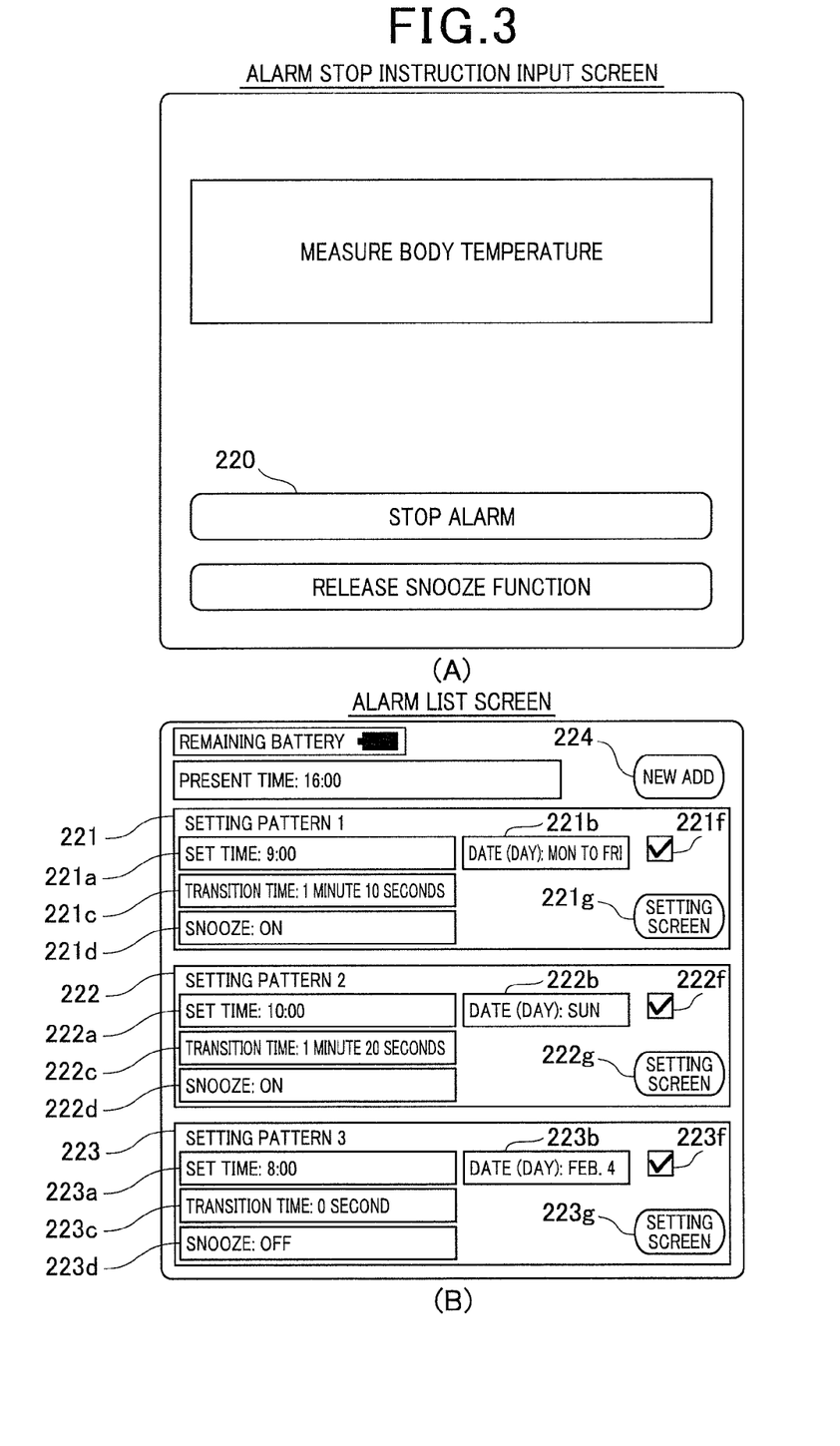
FIG. 3(A) is a figure illustrating an exemplary alarm stop instruction receiving screen displayed on a display of a display unit 22.
FIG. 3(B) is a figure illustrating an exemplary alarm list screen displayed on the display of the display unit 22.

FIG. 3(A) is a figure illustrating an exemplary alarm stop instruction receiving screen displayed on the display of the display unit 22. In the example of FIG. 3(A), an alarm stop instruction button 220 for stopping an alarm is displayed on the screen. When the user designates (taps by a finger, for example) the alarm stop instruction button 220, it is determined that a stop instruction is input by the user.

The data reception control unit 272 transits to a standby state in which measurement data wirelessly transmitted from the thermometer 1 can be received in response to the stopped alarm (which will be called "data reception standby state" below). That is, the data reception control unit 272 sets ON the data reception function of the near-distance wireless communication unit 24 thereby to transit to the data reception standby state with the stopped alarm by the user's stop instruction as a trigger (in other words, with a user-input stop instruction as a trigger). Thereby, user's labor of operation can be efficiently reduced when the portable terminal 2 receives the measurement data from the thermometer 1.

Alarm stop includes "regular stop" and "temporary stop." An alarm is not output again after the alarm is stopped in regular stop. That is, the alarm function is set OFF in regular stop. Therefore, an alarm is not output again until the alarm function is set ON by a user's setting instruction in regular stop. On the other hand, an alarm is output again after a second predetermined time since the alarm is stopped in temporary stop. The re-output function by which the alarm is output again after a second predetermined time since the alarm is stopped is called a snooze function. Temporary stop in the snooze function includes a user's stop instruction and automatic stop without a user's stop instruction within an alarm duration (such as one minute). This snooze function can be set ON/OFF. The number of snoozes and an interval between snoozes can be set in the snooze function. The number of snoozes is the number of times of repeated alarm output. For example, when the number of snoozes is set at 2, the (first) alarm is output again after a second predetermined time (which will be called "snooze time" below) since the alarm is stopped, and the (second) alarm is output again after the snooze time since the first alarm is stopped, and then an alarm is not output. The snooze interval corresponds to the snooze time until an alarm is output again after the alarm is stopped.

The data reception control unit 272 may make a transition to the data reception standby state immediately after an alarm is stopped, or may make a transition to the data reception standby state after a transition time set less than a time required for user's body temperature measurement. The transition time is a time until the transition to the data reception standby state after the alarm is stopped (after the stop of the alarm). By the way, it is desirable that the standby time until the measurement data being actually received after the transition to the data reception standby state is shorter. This is because consumed power of the battery unit 26 is larger in the standby time than in a non-standby time. A user-dependent time such as user's taking and powering on the thermometer is needed until the measurement data starts being received after the alarm is stopped in addition to a time required to measure a body temperature by the thermometer 1. Therefore, in the flow of stop of the alarm, transition to the data reception standby state and start of reception of measurement data, there may be configured such that a time $\Delta t1$ (transition time) until the transition to the data reception standby state after the alarm is topped is controlled to shorten a time $\Delta t2$ (standby time) until the measurement data starts being received after the transition to the data reception standby state.

The transition time $\Delta t1$ is controlled as follows. At first, an initial value of the transition time $\Delta t1$ is set at a time (such as one minute) required to measure a body temperature by the thermometer 1 communicating with the portable terminal 2. Alternatively, the transition time $\Delta t1$ may be initially set at "zero second." Then, a history of receiving of received measurement data from the thermometer 1 is stored in the storage unit 21. The history of receiving of the received measurement data includes a time when an alarm is stopped and a time when a measurement data starts being received. A measurement unit 373 measures a time until measurement data is received after the alarm is stopped based on the history of receiving of the received measurement data. For example, the measurement unit 373 measures a time ($\Delta t1 + \Delta t2$) corresponding to a difference between a time when the alarm is stopped and a time when the measurement data starts being received as a time until the measurement data is received after the alarm is stopped. The thus-measured time is stored as a measurement history in the storage unit 21. Then the setting unit 274 sets a transition time until the transition to the data reception standby state after the alarm is stopped based on the time measured by the measurement unit 273 (or based on the measurement history). For example, assuming that the portable terminal 2 receives measurement data from the thermometer 1 a predetermined number of times (such as five times), it is assumed that the measurement time ($\Delta t1 + \Delta t2$) is of the first time of "1 minute 15 seconds", the second time of "1 minute 20 seconds", the third time of "1 minute 23 seconds", the fourth time of "1 minute 21 seconds" and the fifth time of "1 minute 19 seconds." That is, a history of five measurements is assumed to be stored in the storage unit 21. In this case, the setting unit 274 sets a transition time to the data reception standby state as $\Delta t1$ based on the shortest time of "1 minute 15 seconds" in the measured time ($\Delta t1 + \Delta t2$). For example, the setting unit 274 sets a transition time of "1 minute 10 seconds" to the data reception standby time as $\Delta t1$ in order to take a margin of 5 seconds for the shortest time of "1 minute 15 seconds." Thereby, the standby time $\Delta t2$ until the measurement data is actually received after the transition to the data reception standby state can be shortened. Thus, power saving of the battery unit 26 can be achieved.

Then the setting unit 274 performs various settings on the alarm in response to a user's setting instruction. The alarm setting items include alarm setting time of the alarm, snooze function ON/OFF, number of snoozes, interval between snoozes, and the like as described above. That is, the setting items can be set by the user. By the way, a first predetermined time (which will be called "timeout time" below) until the data reception standby state is released because measurement data cannot be received after the transition to the data reception standby state is previously set at a predetermined time (such as one minute). Then the timeout time may be set by the user. Further, a time until the data reception standby state is released because measurement data cannot be received after the alarm is stopped may be set by the user. The timeout time may be set in response to a user's setting instruction.

When the snooze function is set ON by the setting unit 274, if measurement data is not received (cannot be received) from the thermometer 1 within the timeout time after the transition to the data reception standby state, the data reception control unit 272 keeps the snooze function after the data reception standby state is released. Thereby, an alarm is output again after the snooze time. On the other hand, when the snooze function is set OFF, if measurement data is not received from the thermometer 1 within the timeout time after the transition to the data reception standby state, the setting unit 274 sets ON the snooze function. When measurement data cannot be received, the user is likely to have fallen back to sleep after stopping the alarm. Therefore, if the snooze function is not ON, it is set ON, thereby outputting an alarm again. Thereby, even if the user falls back to sleep after stopping the alarm, it is possible to prevent measurement of a body temperature from being skipped.

Then, when the snooze function is set ON by the setting unit 274, if measurement data is received from the thermometer 1 within the timeout time after the transition to the data reception standby state, the setting unit 274 sets OFF the snooze function. The reception of measurement data indicates that the user is likely to be awake. In this case, the snooze function is set OFF, thereby automatically releasing of the snooze function can be achieved. Thereby, the user's labor of operation of setting OFF the snooze function can be omitted.

The setting contents containing at least the alarm setting time, which are set by the setting unit 274, are stored in the storage unit 21. A plurality of setting contents can be registered in the storage unit 21. In other words, the setting unit 274 can register a plurality of setting patterns. This is because the alarm setting time, the transition time to the data reception standby state or the standby time in the data reception standby state or the like may be different between weekday and holiday, due to difference in days (Monday and Thursday), or due to a presence of event or the like. Further, the history of measuring of measured times measured by the measurement unit 373 is stored in the storage unit 21 per setting contents.

FIG. 3(B) is a figure illustrating an exemplary alarm list screen displayed on the display of the display unit 22. The alarm list screen in FIG. 3(B) indicates that three setting patterns are registered by way of example. The setting content display columns 221 to 223 corresponding to each of the setting patterns display therein, as setting contents, alarm setting times 221a to 223a, date (day) 221b to 223b, transition times 221c to 223c to the data reception standby state, and the snooze function ON/OFF 221d to 223d, respectively. In the example of FIG. 3(B), the setting contents displayed in the setting content display column 221 corresponds to a weekday setting pattern. On the other hand, the setting contents displayed in the setting content display column 222 correspond to a holiday setting pattern. Then, in the example of FIG. 3(B), the different transition times 221c to 223c are set for the three setting contents displayed in the setting content display columns 221 to 223, respectively. The transition time 221c displayed in the setting content display column 221 corresponding to a weekday setting pattern is set at "1 minute 10 seconds." On the other hand, the transition time 222c displayed in the setting content display column 222 corresponding to a holiday setting pattern is set at "1 minute 20 seconds." This indicates that the user feels easier on a holiday than on a weekday and thus a user-dependent time extends. In this way, the transition times can be set for weekday and holiday, thereby enhancing user's convenience. When the transition time to the data reception standby state is set based on a time measured by the measurement unit 273 as described above, the setting unit 274 sets the transmission time to the data reception standby state in the above method for a plurality of setting contents (or a plurality of setting patterns) based on the measurement history stored for a plurality of setting contents. Thereby, after the alarm output according to the setting contents per setting pattern is stopped, the data reception control unit 272 makes a transition to the data reception standby state after the transition time corresponding to the setting contents elapses.

The setting content display columns 221 to 223 are provided with ON/OFF check boxes 221f to 223f, and setting screen display buttons 221g to 223g, respectively. The ON/OFF check boxes 221f to 223f are directed for selecting whether to output an alarm according to the respective setting contents. The setting screen display buttons 221g to 223g are directed for displaying a respective alarm setting screen. For example, when the user designates (instructs to display) the setting screen display button 221g via the operation unit 23, the alarm setting screen is displayed. An alarm setting time and a transition time to the data reception standby state or the like are set via the thus-displayed setting screen. Further, a setting content display column can be added by a new add button 224. Thereby, a setting pattern can be added.

The mobile wireless communication unit 28 makes wireless communication with a base station in a mobile communication network. Thereby, the control unit 27 accesses the information providing server 3 via the network NW and uploads measurement data received from the thermometer 1 on the information providing server 3. Then, for example, a user ID for identifying the user of the portable terminal 2 is added to the measurement data uploaded on the information providing server 3. Further, the control unit 27 acquires analysis data indicating an analysis result of the measurement data from the information providing server 3 via the network NW and displays it on an analysis result screen, for example. Further, the control unit 27 can download the alarm output/data reception control program from the information providing server 3 via the network NW.

The information providing server 3 comprises a storage unit 31, a communication unit 32 and a control unit or the like as illustrated in FIG. 2(C). The information providing server 3 is an exemplary server apparatus according to the present invention. The storage unit 31 is configured of a hard disk drive or the like, for example. The storage unit 31 stores OS (Operating System) and a measurement data analysis program therein. The measurement data analysis program is a program for performing an analysis processing on measurement data received from the portable terminal 2. And the storage unit 31 (exemplary storage means) stores therein measurement data received from the portable terminal 2, and analysis data indicating an analysis result of the measurement data in association with a user ID per user. Further, the storage unit 31 stores the alarm output/data reception control program therein. The communication unit 32 is an interface for connecting to the network NW.

The control unit 33 is configured of CPU, ROM, RAM and the like, for example. The control unit 33 performs an analysis processing on measurement data received from the portable terminal 2 according to the measurement data analysis program stored in the storage unit 31, for example. For example, when measurement data for a predetermined period of time received from the portable terminal 2 is acquired, the control unit 33 calculates an expected next ovulation date and an expected menstruation start date through the analysis processing, and acquires the expected ovulation date and the expected menstruation start date as analysis results. Further, the analysis results may include advice and the like. Then, the control unit 33 generates analysis data indicating the analysis results, and stores it in association with a user ID in the storage unit 31. This analysis data may indicate the analysis result in a calendar or graph, for example. The control unit 33 transmits the analysis data indicating the analysis results of the measurement data corresponding to the user of the portable terminal 2 to the portable terminal 2 via the communication unit 32 and the network NW in response to a request from the portable terminal 2. Thereby, the analysis result screen indicating the analysis results in a calendar or graph is displayed on the display unit 22 in the portable terminal 2. Further, the control unit 33 (exemplary transmission means) transmits the alarm output/data reception control program to the portable terminal 2 via the communication unit 32 and the network NW in response to a request from the portable terminal 2. Further, the alarm output/data reception control program may be configured to be downloaded from a server other than the information providing server 3.

[2. Alarm Output/Data Reception Control Processing in Portable Terminal 2]

Figure 4:
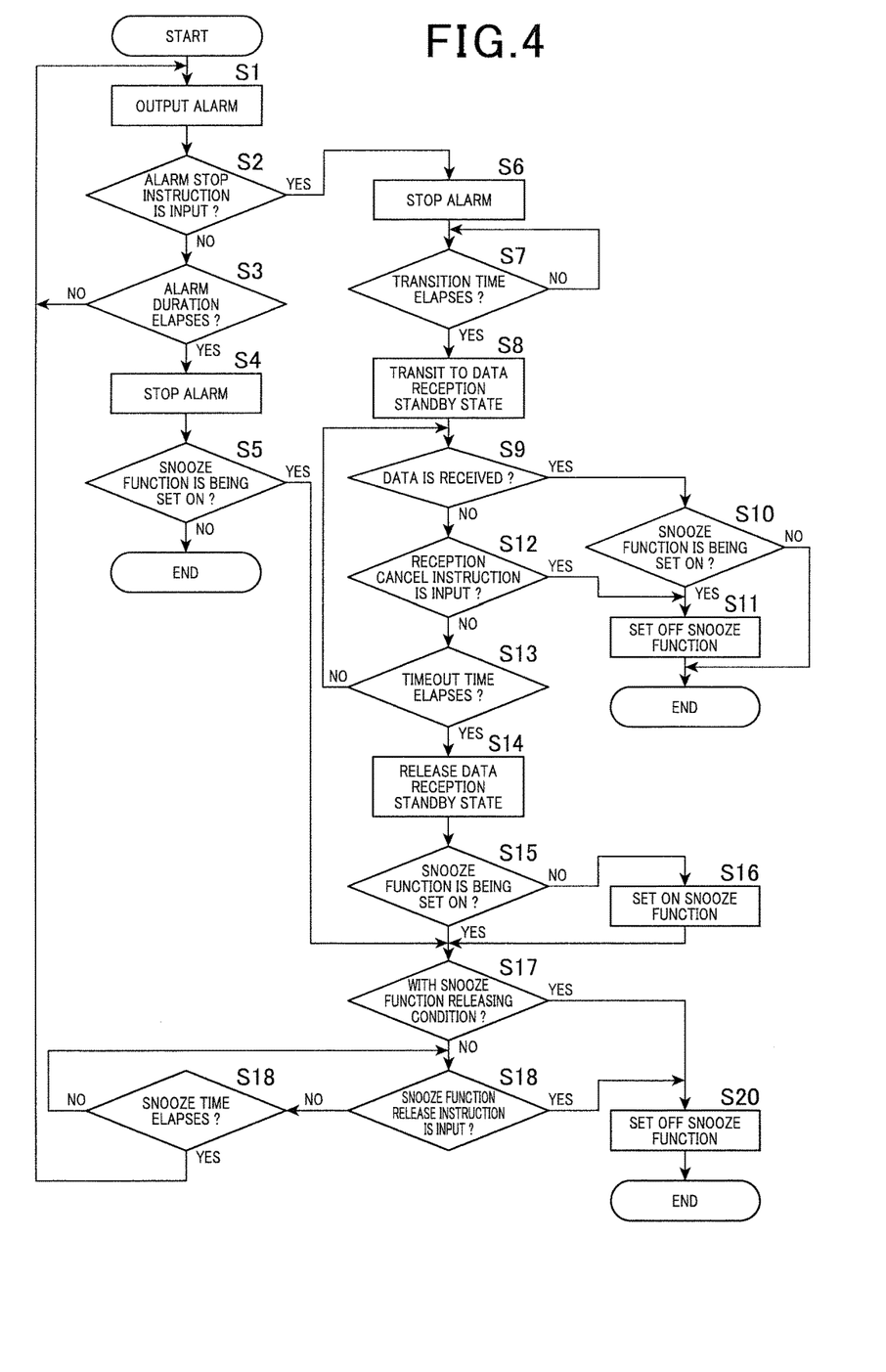
FIG. 4 is a flowchart illustrating an exemplary alarm output/data reception control processing in the control unit 27 in the portable terminal 2.

An exemplary alarm output/data reception control processing in the control unit 27 of the portable terminal 2 will be described below with reference to FIG. 4. FIG. 4 is a flowchart illustrating an exemplary alarm output/data reception control processing in the control unit 27 of the portable terminal 2.

The user activates the alarm output/data reception control program in the portable terminal 2 and sets an alarm before she goes to bed, for example, as a precondition of starting the processing. The processing illustrated in FIG. 4 is started when the alarm set time is reached. When the processing illustrated in FIG. 4 is started, the control unit 27 (alarm output control unit 271) in the portable terminal 2 causes the speaker 25 to output an alarm (step S1). Thereby, an alarm rings from the speaker 25. At this time, the alarm stop instruction receiving screen as illustrated in FIG. 3(A), for example, is displayed on the display of the display unit 22. An elapsed time since the alarm output start point starts being counted. Then the control unit 27 (alarm output control unit 271) determines whether a stop instruction is input by the user while the alarm is being output (or while the alarm is ringing) (step S2). For example, when the alarm stop instruction button 220 displayed on the alarm stop instruction receiving screen illustrated in FIG. 3(A) is designated (tapped by a finger, for example) by the user, it is determined that a stop instruction is input by the user (step S2: YES), and the processing proceeds to step S6. On the other hand, when it is determined that a stop instruction is not input by the user (step S2: NO), the processing proceeds to step S3.

In step S3, the control unit 27 (alarm output control unit 271) in the portable terminal 2 determines whether an alarm duration has elapsed. That is, a determination is made as to whether an elapsed time since the alarm output start point exceeds a preset duration. When it is determined that the alarm duration has not elapsed (step S3: NO), the processing returns to step S1. Thereby, the alarm keeps being output. On the other hand, when it is determined that the alarm duration has elapsed (or has been gone through without a user's alarm stop instruction) (step S3: YES), the processing proceeds to step S4.

In step S4, the control unit 27 (alarm output control unit 271) in the portable terminal 2 causes the speaker 25 to stop outputting the alarm (or to automatically stop the alarm). Then, the control unit 27 (alarm output control unit 271) in the portable terminal 2 determines whether the snooze function is being set ON (step S5). When it is determined that the snooze function is being set ON (step S5: YES), the processing proceeds to step S17. On the other hand, when it is determined that the snooze function is not being set ON (step S5: NO), the processing ends. Further, when it is determined that the snooze function is not being set ON (step S5: NO), the processing may proceed to step S16. In this case, the snooze function is forcibly set ON.

In step S6, the control unit 27 (alarm output control unit 271) causes the speaker 25 to stop outputting the alarm. At this time, an elapsed time since the alarm stop point starts being counted. Then, when the alarm is stopped, the control unit 27 (data reception control unit 272) determines whether the transition time to the data reception standby state has elapsed (step S7). That is, a determination is made as to whether the elapsed time since the alarm stop point has exceeded the transition time previously set by the setting unit 274. When it is determined that the transition time to the data reception standby state has elapsed (step S7: YES), the processing proceeds to step S8. Further, the transition time to the data reception standby state is set as described above, but when the transition time to the data reception standby state is set at "0 second", the control unit 27 may proceed from step S6 to step S8 without performing the processing in step S7.

In step S8, the control unit 27 (data reception control unit 272) makes a transition to the data reception standby state. That is, when the user inputs a stop instruction from the operation unit 23 while the alarm is ringing, the alarm is stopped and the portable terminal 2 transits to the data reception standby state in response to the stop of the alarm (or with the user's input stop instruction as a trigger). At this time, an elapsed time since the transition start point to the data reception standby state starts being counted. The user makes the alarm stop instruction, and then takes the thermometer 1 at her bedside, for example, and measures her body temperature by the thermometer 1. Then, when completing the body temperature measurement, the thermometer 1 wirelessly transmits measurement data indicating the measured body temperature to the portable terminal 2 in the data reception standby state.

Then, the control unit 27 (data reception control unit 272) determines whether the measurement data has been wirelessly received from the thermometer 1 (step S9). When it is determined that the measurement data has been wirelessly received from the thermometer 1 (step S9: YES), the processing proceeds to step S10. On the other hand, when it is determined that the measurement data has not been wirelessly received from the thermometer 1 (step S9: NO), the processing proceeds to step S12.

In step S10, the control unit 27 (data reception control unit 272) determines whether the snooze function is being set ON. When it is determined that the snooze function is being set ON (step S10: YES), the control unit 27 (setting unit 274) sets OFF the snooze function (step S11), and ends the processing. When the processing illustrated in FIG. 4 ends in this way, the control unit 27 accesses the information providing server 3 from the mobile wireless communication unit 28 via the network NW, and transmits the measurement data received from the thermometer 1 to the information providing server 3. On the other hand, when it is determined that the snooze function is not being set ON (step S10: NO), the snooze function keeps being set OFF, and the processing ends.

In step S12, the control unit 27 (data reception control unit 272) determines whether a reception cancel instruction has been input by the user. When it is determined that a reception cancel instruction has been input by the user (step S12: YES), the processing proceeds to step S11. On the other hand, when it is determined that a reception cancel instruction has not been input by the user (step S12: NO), the processing proceeds to step S13.

In step S13, the control unit 27 (data reception control unit 272) determines whether the timeout time has elapsed. That is, a determination is made as to whether the elapsed time since the transition start point to the data reception standby state has exceeded the timeout time previously set by the setting unit 274. When it is determined that the timeout time has not elapsed (step S13: NO), the processing returns to step S9, where the data reception standby state is kept. On the other hand, when it is determined that the timeout time has elapsed (step S13: YES), the processing proceeds to step S14.

In step S14, the control unit 27 (data reception control unit 272) releases the data reception standby state. For example, the control unit 27 (data reception control unit 272) sets OFF the data reception function of the near-distance wireless communication unit 24 thereby to release the data reception standby state. Then, the control unit 27 (data reception control unit 272) determines whether the snooze function is being set ON (step S15). When it is determined that the snooze function is not being set ON (step S15: NO), the control unit 27 (setting unit 274) sets ON the snooze function (step S16), and proceeds to step S17. That is, the snooze function is forcibly set ON. On the other hand, it is determined that the snooze function is being set ON (step S15: YES), the snooze function keeps being set ON and the processing proceeds to step S17. Further, the control unit 27 (data reception control unit 272) may release the data reception standby state immediately after the snooze function is set ON (step S16) (or between step S16 and step S17), not in step S14.

In step S17, the control unit 27 (alarm output control unit 271) determines whether a condition for releasing the snooze function is met (provided). For example, when the number of snoozes (that is, the number of times of alarm re-output) reaches the set number of snoozes after the processing illustrated in FIG. 4 is started, it is determined that the condition for releasing the snooze function is met. When it is determined that the condition for releasing the snooze function is not met (step S17: NO), the processing proceeds to step S18. On the other hand, when it is determined that the condition for releasing the snooze function is met (step S17: YES), the snooze function is set OFF (step S20) and the processing ends.

In step S18, the control unit 27 (alarm output control unit 271) determines whether a snooze function release instruction has been input by the user. When it is determined that a snooze function release instruction has been input by the user (step S18: YES), the snooze function is set OFF (step S20) and the processing ends. On the other hand, when it is determined that a snooze function release instruction has not been input by the user (step S18: NO), the processing proceeds to step S19.

In step S19, the control unit 27 (alarm output control unit 271) determines whether the snooze time has elapsed. That is, a determination is made as to whether an elapsed time since the alarm stop point has exceeded the snooze previously set by the setting unit 274. When it is determined that the snooze time has not elapsed (step S19: NO), the processing returns to step S18. On the other hand, when it is determined that the snooze time has elapsed (step S19: YES), the processing returns to step S1 and the alarm is output again.

As described above, according to the present embodiment, the portable terminal 2 is configured to cause the speaker 25 to output an alarm at a preset time, to cause the speaker 25 to stop outputting the alarm when a stop instruction is input by the user while the alarm is being output, and to transit to a state in which measurement data wirelessly transmitted from the thermometer 1 (data reception standby state) in response to the stop of the alarm, and thus user's labor of operation can be efficiently reduced when the portable terminal 2 receives the measurement data from the thermometer 1. That is, the user can make a transition to the data reception standby state in which measurement data can be wirelessly received from the thermometer 1 by only making an instruction of stopping the ringing alarm immediately after she wakes up. Thus, it is possible to reduce troublesome steps of activating the application program immediately after the user wakes up and receiving measurement data from the thermometer 1. Thereby, in every morning, it is possible to promote measurement data to be transferred from the thermometer 1 to the portable terminal 2 after a body temperature is measured. Further, the alarm function of the thermometer 1 can be omitted.

Further, according to the present embodiment, it is possible to omit user's labor of for startup of the above-described application program and log-in which have been required in the conventional technique. According to the above embodiment, it is possible to shorten a time taken for activating the application program, for logging in and for performing a processing of making a transition to the data reception standby state, which have been required in the conventional technique. In particular, a time required for a processing of making a transition to the data reception standby state can be reduced because when the alarm is stopped, the data reception standby state is brought while the user is measuring a body temperature and thus measurement data can be immediately transferred to the portable terminal 2.

In the above embodiment, the portable terminal 2 may be configured to transmit a signal of instructing to make a transition to a state in which a body temperature can be measured to the thermometer in a state in which a signal from the portable terminal 2 can be received with the stop of the alarm as a trigger (in response to the stop of the alarm). In this case, it is assumed that the thermometer has three states. The first state is that the power supply is completely in the OFF state. The second state is that a signal of instructing to make a transition to a state in which a body temperature can be measured can be received but a circuit or the like for measuring a body temperature is not conductive. Alternatively, the second state is that a signal of instructing to make a transition to a state in which a body temperature can be measured is received and all the circuits including the body temperature measurement circuit are conductive. The third state is that a body temperature can be measured. When receiving a signal transmitted from the portable terminal 2, the thermometer transits from the second state to the third state. With such a structure, a user's step of setting ON the thermometer can be omitted.

The above embodiment has been described with the thermometer as a measurement instrument by way of example, but the measurement instrument may be any measurement instrument capable of measuring biological information such as blood pressure and heart rate.

DESCRIPTION OF REFERENCE NUMERALS

1: Thermometer
2: Portable terminal
3: Information providing server
NW: Network
S: Information providing system

The invention claimed is:

1. An information processing apparatus comprising:
at least one memory operable to store program code;
at least one processor operable to access said memory and read said program code and operate as instructed by said program code, said program code including:
receive code configured to cause said at least one processor to receive a biological information, wirelessly transmitted from a measurement instrument being used by a user to measure the biological information, when a data reception function is set ON to receive data from the measurement instrument through wireless transmission;
output control code configured to cause said at least one processor to output an alarm at a preset time;
stop control code configured to cause said at least one processor to, when a stop instruction is input by the user while the alarm is being output, stop the output of the alarm; and
transition control code configured to cause said at least one processor to automatically make a transition, in response to the output of the alarm being stopped, from a non-standby state, which is a first power mode and in which the data reception function is set OFF, to a standby state, which is a second power mode and in which the data reception function is set ON, such that the biological information wirelessly transmitted from the measurement instrument, is received by the receive code, the first power mode having lower power consumption than the second power mode.

2. The information processing apparatus according to claim 1, wherein when the biological information is not received from the measurement instrument within a first predetermined time after the transition to the standby state, the output control code is further configured to cause said at least one processor to output alarm again after a second predetermined time.

3. The information processing apparatus according to claim 1, further comprising a first setting code configured to cause said at least one processor to set ON or OFF a re-output function of outputting the alarm again after a second predetermined time after the alarm is stopped,
wherein when the re-output function is set ON, if the biological information is received from the measurement instrument within a first predetermined time after the transition to the standby state, the first setting code is further configured to cause said at least one processor to set OFF the re-output function.

4. The information processing apparatus according to claim 1, further comprising:
measurement code configured to cause said at least one processor to measure a time until the biological information is received after the alarm is stopped; and
second setting code configured to cause said at least one processor to set a transition time until the standby state is brought after the alarm is stopped based on the time measured by the measurement code,
wherein when the transition time set by the second setting code elapses after the alarm is stopped, the transition control code is further configured to cause said at least one processor to make the transition to the standby state in which the biological information is receivable.

5. The information processing apparatus according to claim 4, wherein the at least one memory is configured to store a history of times measured by the measurement code for a plurality of setting contents containing at least an alarm setting time,
wherein the second setting code is further configured to cause said at least one processor to set the transition time for the setting contents based on the measurement history, and
when the transition time corresponding to the setting contents elapses after the alarm output according to the setting contents by the output control code is stopped, the transition control code is further configured to cause said at least one processor to make the transition to the standby state in which the biological information is receivable.

6. The information processing apparatus according to claim 1, further comprising a second setting code configured to cause said at least one processor to set a transition time until the standby state is brought after the alarm is stopped based on at least a time required to measure the biological information by the measurement instrument,
wherein when the transition time set by the second setting code elapses after the alarm is stopped, the output control code is further configured to cause said at least one processor to make the transition to the standby state in which the biological information is receivable.

7. The information processing apparatus according to claim 1, wherein the alarm is a wake-up alarm.

8. An information processing method performed by a computer, including at least one processor, the method comprising:
receiving a biological information, wirelessly transmitted from a measurement instrument being used by a user to measure the biological information, when a data reception function is set ON to receive data from the measurement instrument through wireless transmission:
outputting, by said at least one processor, an alarm at a preset time;
when a stop instruction is input by the user while the alarm is being output, stopping, by said at least one processor, the alarm; and
automatically transitioning, by said at least one processor, in response to the stop of the alarm, from a non-standby state, which is a first power mode and in which the data reception function is set OFF, to a standby state, which is a second power mode and in which the data reception function is set ON, such that the biological information wirelessly transmitted from the measurement instrument is received, the first power mode having lower power consumption than the second power mode.

9. A server apparatus to which an information processing apparatus is connectable via a network, including at least one processor, comprising:
a memory configured to store a program code; and
the at least one processor operable to access said memory and read said program code and operate as instructed by said program code, said program code including:

receive code configured to cause said at least one processor to receive a biological information, wirelessly transmitted from a measurement instrument being used by a user to measure the biological information, when a data reception function is set ON to receive data from the measurement instrument through wireless transmission;

output control code configured to cause said at least one processor to output an alarm at a preset time, stop control code configured to cause said at least one processor to, when a stop instruction is input by the user while the alarm is being output, stop the output of the alarm, and transition control code configured to cause said at least one processor to automatically make a transition, in response to the output of the alarm being stopped, from a non-standby state, which is a first power mode and in which the data reception function is set OFF, to a standby state, which is a second power mode and in which the data reception function is set ON, such that the biological information wirelessly transmitted from the measurement instrument is received, the first power mode having lower power consumption than the second power mode; and a transmitter, within said at least one processor, that transmits the information processing program to the information processing apparatus in response to a request from the information processing apparatus capable of executing the information processing program.

* * * * *